United States Patent [19]
Haber et al.

[11] Patent Number: 4,710,179
[45] Date of Patent: Dec. 1, 1987

[54] SNAP-ON VERNIER SYRINGE

[75] Inventors: Terry M. Haber, Lake Forest; Clark B. Foster, El Toro; John A. Lewis, Jr., Costa Mesa, all of Calif.

[73] Assignee: Habley Medical Technology Corporation, Laguna Hills, Calif.

[21] Appl. No.: 923,572

[22] Filed: Oct. 27, 1986

[51] Int. Cl.⁴ ............................................ A61M 5/00
[52] U.S. Cl. ................................................ 604/211
[58] Field of Search ............... 604/211, 218, 224, 208, 604/209, 210

[56] References Cited
U.S. PATENT DOCUMENTS

| | | | |
|---|---|---|---|
| 4,470,317 | 9/1984 | Sabloewski et al. | 604/211 |
| 4,498,904 | 2/1985 | Turner et al. | 604/211 |
| 4,568,335 | 2/1986 | Updike et al. | 604/211 |
| 4,583,974 | 4/1986 | Kokernak | 604/211 |

Primary Examiner—John D. Yasko
Attorney, Agent, or Firm—Morland C. Fischer

[57] ABSTRACT

A low cost, easy to use, snap-on, linear-to-vernier syringe by which a volume of material may be controllably and accurately delivered to a recipient. By virtue of the present invention, a piston supporting collar member may be securely snapped into releaseable engagement with a conventional, disposable syringe cylinder to complete the syringe assembly. Moreover, the conventional syringe cylinder is thereby converted into a precisely accurate pipetting cylinder to control the infusion of highly potent, dosage sensitive, radioactive, or expensive drugs, and the like, without requiring any modification to the cylinder. The syringe assembly is particularly adapted to permit rapid switching between freely rotated and incrementally rotated modes of operation, whereby a predetermined volume of material may be selectively imparted from the syringe cylinder, either continuously or in discrete and precisely calibrated increments.

14 Claims, 7 Drawing Figures

SNAP-ON VERNIER SYRINGE

BACKGROUND OF THE INVENTION

1. Field of the Invention

This invention relates to a snap-on, linear-to-vernier syringe assembly which provides a physician with the ability to controllably infuse a precisely accurate, calibrated volume of a highly potent, dosage sensitive, radioactive, or expensive drug, or the like, either continously or incrementally.

2. Prior Art

As will be appreciated by those skilled in the art, a physician is often required to administer to a recipient, by way of a hypodermic syringe, a doseage comprising a highly potent, dosage sensitive, radioactive, or expensive drug. In some cases, extreme care must be taken to avoid an under or over dose of an urgently needed drug, so that a prescribed volume of drug can be precisely imparted according to the medical requirements of the recipient. In other cases, particularly where the drug is rare and/or expensive, it is desirable to avoid waste, whereby to minimize cost and conserve available supplies of such drug.

However, there is no known inexpensive, easy to use and readily available syringe by which to permit a physician to controllably deliver to a recipient a predetermined and precisely accurate volume of material. Some attempts have been made to resolve this problem by way of combining special metering apparatus with the conventional syringe. Other attempts have required that the conventional syringe cylinder be modified. Unfortunately, all of these attempts involve the use of relatively complex and/or expensive equipment which may prove to be time consuming to assemble and difficult to operate. Consequently, the cost and inconvenience associated with such equipment is undesirable to both the recipient and physician.

SUMMARY OF THE INVENTION

Briefly, and in general terms, an inexpensive and reliable snap-on, linear-to-vernier syringe is disclosed which overcomes the aforementioned problems often associated with conventional syringes. The syringe of the present invention comprises a threaded piston, a collar having a threaded opening for receiving the piston therethrough, and a conventional syringe cylinder from which a physician may controllably and selectively impart material to a recipient. The collar is provided with a centrally disposed opening through which an end of the syringe cylinder may be inserted, so that the cylinder is releaseably snapped into locking engagement with the collar and the threaded piston is inserted for rotational and linear, axial movement through the cylinder. The physician operates a cylinder removal pin at the collar for moving an associated catch into or out of a seat formed in the collar core. With the catch seated, the syringe cylinder may be connected to or disassembled from the collar by way of the central opening. An unseated catch blocks both the removal of the syringe cylinder from the collar and the piston from the cylinder.

A mode selector button is also located at the collar so that the presently disclosed syringe is capable of infusing material in either a freely rotated or incrementally rotated mode of operation. Thus, and by virtue of the present invention, a conventional syringe cylinder may be converted into a precisely accurate pipetting cylinder to control the infusion of a highly potent, dosage sensitive, radioactive, or expensive drug or the like, either continously or in discrete, precisely calibrated increments. More particularly, when the physician moves the mode selector button to the incrementally rotated switch position, a detent tooth is received in one of the pair oppositely aligned, longitudinally extending locking grooves formed in the position so as to prevent rotation of the piston. The physician then depresses a piston release locking button which causes the detent tooth to move out of receipt by the piston groove. The physician rotates the piston while depressing the piston release button to establish a corresponding linear movement of the piston through the syringe cylinder. Depending upon the direction of rotation, the physician may withdraw the piston from the cylinder of infuse a precisely accurate volume of material to a recipient. The physician continues to rotate the piston (e.g. a total of 180°) until the second of the pair of grooves is positioned to receive the detent tooth and prevent further piston rotation. The periodic receipt of the tooth in successive locking grooves provides an automatic locking function and a fail-safe means by which to assure that the same, calibrated volume of material (e.g. 0.25 cc) is dispensed from the syringe cylinder during each 180° rotation of the piston.

Movement of the mode selector button to the automatic switch position causes a corresponding movement of an associated dog through a trough formed in the collar core. The physician first depresses the piston release button to move the detent tooth out of a piston groove. The physician moves the mode selector button to the freely rotated switch position which advances the dog to a location between the detent tooth and the piston, whereby to block the return of the tooth to the groove. Accordingly, the physician may freely rotate the piston to either quickly and easily remove the piston from the syringe cylinder or continously dispense material to the recipient.

DESCRIPTION OF THE PREFERRED EMBODIMENT

Figure 1:
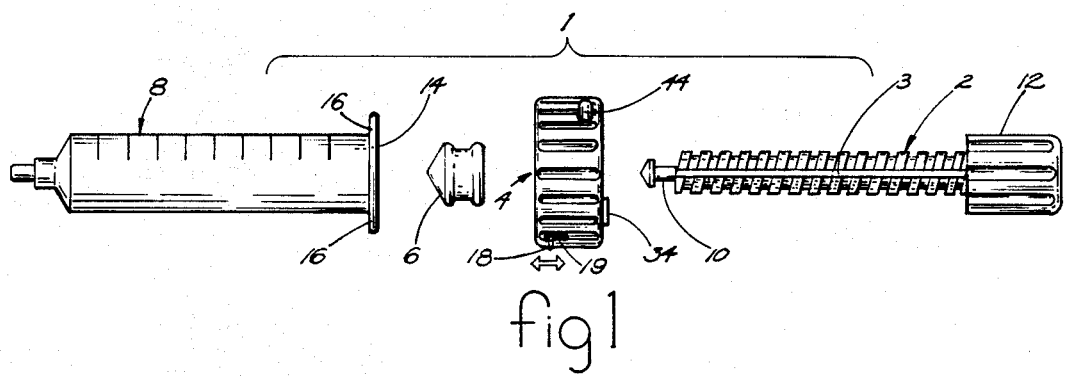
FIG. 1 shows an exploded view of the snap-on vernier syringe which forms the present invention.

The snap-on vernier syringe 1 of the present invention is best described while referring to the drawings. In FIG. 1, there is shown an exploded view of a syringe assembly comprising a threaded piston 2, a collar 4, a flexible piston sealing head 6, and a conventional calibrated syringe cylinder 8. In the assembled relationship of FIG. 2, and referring concurrently to FIGS. 1 and 2 of the drawings, the threaded piston 2 is received in a centrally disposed, threaded opening formed in collar 4.

The piston 2 has a pair of locking grooves 3 extending longitudinally along the the threaded body thereof. The piston head 6 is secured to a terminal 10 formed at the distal end of piston 2, and a piston control knob 12 is affixed to the proximal end of piston 2. The piston head 6 is inserted through the open mouth 14 of syringe cylinder 8, so that the piston 2 may be controllably moved through syringe cylinder 8 in a manner and for a purpose that will be described in greater detail hereinafter.

In accordance with an important feature of the present invention, the collar 4 is snapped into releasable engagement with the lips 16 which surround the mouth 14 of syringe cylinder 8. For disposable usages, the syringe cylinder 8 is preferably fabricated from a clear, non-breakable plastic material. In accordance with another important, soon to be described feature of the present invention, the disclosed vernier syringe 1 is adapted to quickly and easily convert the conventional syringe cylinder 8 into a precisely accurate pipetting cylinder to control the infusion of highly potent, dosage sensitive, radioactive, or very expensive materials (e.g. drugs) without requiring that modifications be made to the cylinder 8.

The aforementioned advantages of the present invention are now described in detail while referring to FIGS. 3–6 of the drawings where the syringe collar 4 is illustrated. As previously disclosed, collar 4 has a centrally disposed, threaded opening 9 for receipt therethrough of the threaded piston 2. Collar 4 is provided with a manually accessible, spring biased cylinder removal pin 18 which is adapted to ride up and down through a slot 19 (of FIG. 1) formed in a side of collar 4 to selectively secure or release the connection between the lips 16 of syringe cylinder 8 and the collar 4. More particularly, and referring specifically to FIG. 3 of the drawings, an access opening 20 is formed in the bottom face 22 of collar 4. Opening 20 has a shape which generally conforme to the shape of the lips 16 which surround the mouth of syringe cylinder 8. Spaced above the bottom face 22 and accessible through the opening 20 formed therein is the core 24 of collar 4. A catch member 26 is interconnected to the aforementioned piston removal pin 18 and adapted to move between the collar core 24 and the bottom face 22 when the pin 18 rides through the slot 19 formed in collar 4. That is, with the cylinder removal pin 18 in a lower-most position in slot 19, catch member 26 is recessed within a seat 28 formed in collar core 24. With the cylinder removal pin 18 raised to the upper-most position in slot 19, the catch member 26 is correspondingly raised out of its seat in the core 24 and moved upwardly into the space between the bottom face 22 and the core 24 of collar 4.

Figure 2:
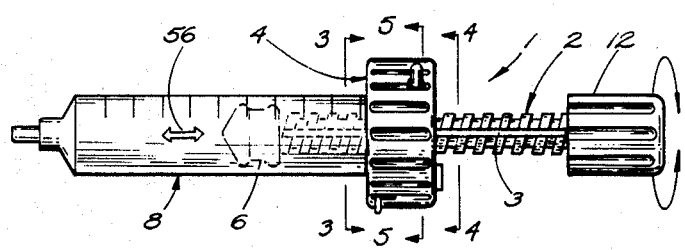
FIG. 2 shows the syringe of FIG. 1 in the assembled relationship.

In operation, and to complete the assembled syringe relationship of FIG. 2, the physician places the collar 4 over the syringe cylinder 8, so that the cylinder lips 16 are received in the access opening 20 of collar 4 and the piston 2 is extended into and past the mouth of cylinder 8. The cylinder removal pin 18 is moved against the bias of its associated spring (designated 58 in FIG. 5) and held at its lower-most position in slot 19, whereby catch member 26 is seated within the collar core 24. The physician then rotates the syringe cylinder 8 so that the lips 16 thereof are rotated through the space between the bottom face 22 and the core 24 of collar 4 and past the recessed catch 26. At this time, the physician releases the cylinder removal pin 18. The normal bias of the spring automatically returns the cylinder removal pin 18 to its upper-most position in slot 20. Accordingly, the catch member 26 is moved out of its seat 28 in the core 24 and into the space between the bottom face 22 and core 24 of collar 4. The catch member 26 therefore performs a positive locking function by blocking the path of rotation of the lips 16 and preventing the lips from being inadvertently rotated in a direction back towards the opening 20. Hence, the collar 4 will be securely connected to the syringe cylinder 8 whereby to permit the locking of a hypodermic needle tip to the syringe cylinder and avoid the accidental loss of highly potent, rare and/or expensive materials to be infused from cylinder 8.

In the event that the physician wishes to remove the syringe cylinder 8 from the collar 4 (for the purpose of either disposing the cylinder or substituting a different cylinder), the cylinder removal pin 18 is once again moved to and held at its lower-most position in slot 19, whereby the catch member 26 is returned to its recessed seat 28 to be moved out of the way of the lips 16 of syringe cylinder 8. The physician rotates cylinder 8 so that the lips 16 thereof are aligned below the opening 20 in the bottom face 22 of collar 4. The lips 16 of the cylinder 8 may then be easily withdrawn through the opening 20, whereupon the cylinder 8 may be separated from the piston 2.

Figures 3, 4, 6:
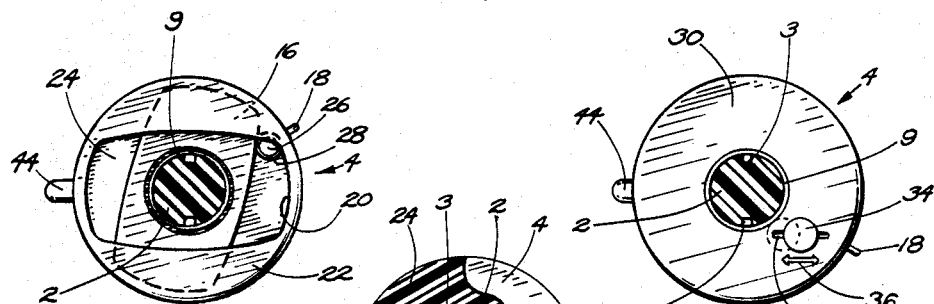
FIG. 3 is a cross-section taken along lines 3—3 of FIG. 2.
FIG. 4 is a cross-section taken along lines 4—4 of FIG. 2.
FIG. 6 details the operation of the linkage assembly illustrated in FIG. 5.

Referring now to FIG. 4 of the drawings, the top face 30 of the collar 4 is shown with the aforementioned threaded opening 9 extending therethrough for receipt of piston 2. A narrow slot 32 is formed in the top face 30. Extending outwardly from slot 32 is a manually accessible mode selector button 34. The mode selector button 34 is slideable through slot 32 (in the direction of reference arrow 36) to either a freely rotated or incrementally rotated switch position. As will be disclosed in greater detail when referring to FIG. 5, the mode selector button 34 operates in combination with a piston release button 44, so that the rotational movement of the threaded piston 2 through the threaded opening 9 and the corresponding linear, axial movement of the piston head 6 through syringe cylinder 8 can be selectively controlled. In this manner, the piston movement is stabilized against the effects of suction or back pressure to avoid resulting variances in fluid pressures.

Figure 5:
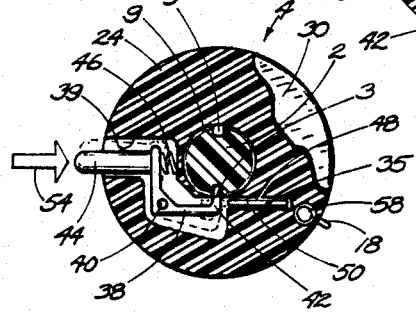
FIG. 5 is a cross-section taken along lines 5—5 of FIG. 2.

The means by which to enable the physician to selectively control the rotation of threaded piston 2 and linear, axial movement of piston head 6 is mechanical linkage housed within the collar 4 and now described while referring to FIG. 5 of the drawings. More particularly, the mechanical linkage includes a rotatable detent arm 38 which is located within a cavity 39 formed in the collar core 24. Detent arm 38 is mounted upon a pivot pin 40 which extends upwardly through cavity 39 and around which such detent arm is adapted to rotate. Detent arm 38 has a relatively narrow detent tooth 42 formed at one end thereof. An opening (not shown) is formed through the other end of detent arm 38 for receiving the stem of the aforementioned piston release button 44. The rotational movement of the detent arm 38 around pivot pin 40 is controlled by the release button 44 and a coaxially aligned compression spring 46 which surrounds the stem of button 44 between detent arm 38 and a wall of cavity 39. Release button 44 extends from detent arm 38 and along cavity 39 to a manually accessible location at a side of collar 4.

Coextensively formed with cavity 39 is a narrow trough 48. Resting within and slideable through the trough 48 is a dog 50. The dog 50 has a small aperture formed therein for receiving the stem 35 of the aforementioned mode selector button (designated 34 in FIGS. 1 and 4). Referring concurrently to FIGS. 4 and 5, and in the assembled collar relationship, the slot 32 formed in the top face 30 of collar 4 is positioned above the trough 48 formed in the collar core 24. Therefore, when the physician moves the mode selected button 34 along slot 32 (in one of the directions designated by reference arrows 52), the dog 50, which is connected to selector button 34 by way of stem 35, moves in a corresponding direction through trough 48 for a purpose which will now be disclosed.

In operation, and still referring concurrently to FIGS. 4 and 5 of the drawings, with the mode selector button 34 moved to an incrementally rotated switch position along slot 32, the dog 50 is moved to a corresponding position in trough 48 out of the way of the detent tooth 42 of detent arm 38 (best illustrated in FIG. 5). In the incrementally rotated mode of operation, the compression spring 46 biases the detent arm 38 at a first position in cavity 39 such that the detent tooth 42 is received within one of the pair of longitudinal locking grooves 3 which extends along the threaded body of piston 2. The receipt of the detent tooth 42 in a groove 3 prevents both the rotation of piston 2 and the linear movement of piston head 6 through the syringe cylinder 8.

In the incrementally rotated mode of operation, when the physician wishes to accurately dispense material from syringe cylinder 8 in discrete, calibrated increments, he depresses the piston release button 44 (in the direction of reference arrow 54) against the bias of spring 46. The depression of release button 44 causes a corresponding rotation of detent arm 38 around pivot pin 40 (shown in phantom in the rotated position), such that the detent tooth 42 is moved out of the groove 3 in piston 2. The physician rotates the piston control knob 12 (of FIGS. 1 and 2) of threaded piston 2 while releasing the release button 44. Each degree of rotation of control knob 12 and threaded piston 2 causes a corresponding linear movement of the piston head 6 through the syringe cylinder 8 in one of the directions represented by reference arrows 56 (of FIG. 1). In this manner, and depending upon the direction of rotation of control knob 12, the physician may either withdraw the piston 2 from the cylinder 8 or infuse a precisely accurate volume of material from the cylinder to a recipient.

The physician continues to rotate the control knob 12 and piston 2 during the incrementally rotated mode of operation until the second of the pair of grooves 3 is moved into position to receive the detent tooth 42. The normal bias of spring 46 rotates the detent arm 38 around pivot pin 40, such that the detent tooth is automatically moved into the second groove 3 of piston 2 to, once again, prevent any further rotation of piston 2 and linear movement of piston head 6. Because the pair of longitudinally extending grooves 3 are at opposite sides of piston 2, the detent tooth 42 will be received in one of the grooves 3 after each 180 rotation of the piston 2 in the manual mode of operation. Thus, the receipt of the detent tooth 42 in successive ones of the grooves 3 provides an automatic locking feature and a fail-safe mechanical monitoring and drug infusion means by which to assure that the same, precisely measured volume of material is dispensed from the syringe cylinder during each 180 rotation of piston 2.

In accordance with a preferred embodiment of the invention, each 180° rotation of the threaded piston 2 causes a linear movement of the piston head 6 a particular distance through the syringe cylinder so as to dispense 0.25 cc. of material. Of course, the pitch of the threaded piston 2 and/or the inside diameter of the syringe-cylinder can be varied so that different volumes of material are dispensed with each 180° rotation of the piston. However, by dispensing 0.25 cc. during each 180° rotation (or 0.50 cc. during each complete 360° rotation), the volume of material dispensed will correspond with the calibration lines typically marked on the conventional 10 cc. syringe cylinder 8. In this manner, and by virtue of the previously described self-locking feature provided by receipt of detent tooth 42 within a piston groove 3, the physician may mechanically and visually monitor the volume of material being dispensed, so as to prevent waste and avoid infusing under and over-doses of highly potent, critically needed, rare or expensive drugs.

In the freely rotated mode of operation, when the physician wishes to rotate threaded piston 2 to either continuously dispense material from the syringe cylinder or rapidly disassemble the syringe assembly 1, he depresses the piston release button 44 (in the direction of reference arrow 54) against the bias of spring 46. The depression of locking button 44 causes a corresponding rotation of detent arm 38 around pivot pin 40 such that the detent tooth 42 is moved out of the locking groove 3 in piston 2. With the locking button 44 depressed and the detent tooth 42 moved out of groove 3, the mode selector button 34 is moved away from the incrementally rotated switch position and into the freely rotated switch position at an opposite end of slot 32. The movement of mode selector button 34 causes a corresponding movement of the dog 50 through the trough 48 to a location between detent tooth 42 and piston 2 (best illustrated in FIG. 6). Hence, the dog 50 functions as a stop and prevents the return of detent tooth 42 to a groove 3 in piston 2. Therefore, in the freely rotated mode of operation, and as long as the dog 50 is located in a blocking position between the tooth 42 and the piston 2, the physician may freely rotate piston control knob 12 and threaded piston body 2 in either rotational direction in order to quickly and easily remove the piston or continuosly dispense material from the syringe cylinder.

Should the physician wish to return to the incrementally rotated mode of operation, he simply moves the mode selector button 34 out of the freely rotated switch position and along slot 32 towards the incrementally rotated switch position. The movement of mode selector button 34 along slot 32 causes a corresponding movement of the dog 50 through trough 48 and away from detent tooth 42. Accordingly, with dog 50 moved out of the blocking position, the normal bias of spring 46 automatically rotates the detent arm 38, such that detent tooth 42 is returned to a locking groove 3 in piston 2, whereupon the syringe assembly 1 is adapted for operation in the incrementally rotated mode of operation, in the manner previously described.

Referring once again to FIG. 5, and as previously disclosed when referring to FIG. 3, the physician may move a cylinder removal pin 18 so as to selectively secure or release the connection of the lips of syringe cylinder 8 to the syringe collar 4. As was also previously disclosed, the movement of pin 18 is controlled by a spring. Such a spring 58 is located in an aperture which extends from the top face 30 of collar 4 and through the collar core 24 to the catch member 26 (in FIG. 3). Accordingly, spring 58 normally biases the catch member 26 out of its seat 28 in the collar core 24 so as to block any rotational movement therepast of the syringe lips (designated 16 in FIG. 3). When the physician moves pin 18 through slot 19 (of FIGS. 1 and 2), the catch member 26 is correspondingly moved against the bias of spring 58 to be received within its seat, so that the cylinder lips 16 can be rotated therepast when the syringe cylinder 8 is to be secured to or released from the syringe collar 4 by way of the access opening 20 (of FIG. 3).

Figure 7:
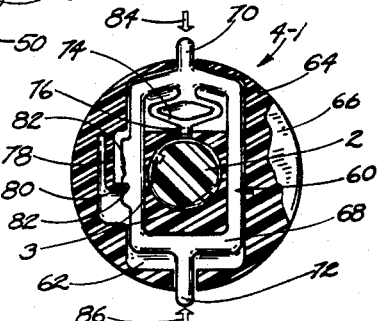
FIG. 7 shows an alternative embodiment of the present invention.

An alternate collar 4-1 for forming the vernier syringe assembly 1 of FIGS. 1 and 2 is shown in FIG. 7 of the drawings. The mechanical linkage previously described when referring to collar 4 of FIG. 5 is replaced by a one-piece actuator 60. Actuator 60 is received in and slideable through a cavity 62 formed in the core 64 below the top face 66 of collar 4-1. Actuator 60 is preferably fabricated from a flexible material such as plastic, or the like.

Actuator 60 comprises a generally rectangular body 68. Piston locking and releasing buttons 70 and 72 extend outwardly and in opposite directions so as to be manually accessible at opposite ends of the actuator body 68. Coextensively formed with piston locking button 70 at one end of actuator body 68 is a bellows-type spring member 74. A detent tooth 76 projects inwardly from the spring member 74 towards the centrally disposed piston 2. The detent tooth 76 is sized so as to be received within each of the pair of locking grooves 3 formed in piston 2. Coextensively formed with the core 64 of collar 4-1 and extending through cavity 62 is a locking arm 78. Locking arm 78 has a locking finger 80 which is snapped into one of a pair of notches 82 and 83 formed in an adjacent side of actuator body 68. The particular notch 82 or 83 which receives the locking finger 80 is dependent upon the location of the actuator 60 within cavity 62. That is, with the actuator 60 moved to a first end of cavity 62 (as illustrated in FIG. 7), the locking finger 80 of locking arm 78 is snapped into a first notch 82 to prevent the lateral movement of actuator 60 through cavity 62. With the actuator 60 moved to the opposite end of cavity 62, the locking finger 80 is snapped into the second notch 83 to prevent an unintended return of actuator 60 to the first cavity end.

To place the syringe in the freely rotated mode of operation, the physician depresses piston release button 72 in the direction of reference arrow 86 to force actuator 60 to slide to the first end of cavity 62 (i.e. at the location illustrated in FIG. 7). In the freely rotated mode, the spring 74 is relaxed, such that locking finger 80 is snapped into notch 82 and the detent tooth 76 is spaced away from piston 2 and out of the grooves 3. Accordingly, the physician is free to continuously rotate the piston 2 by turning control knob 12 (of FIGS. 1 and 2) in the manner and for the purpose that were earlier described.

To place the syringe in the incrementally rotated mode of operation, the physician depresses piston locking button 70 in the direction of reference arrow 84 to force actuator 60 to slide to the opposite end of cavity 62. In the incrementally rotated mode, the spring is compressed, such that locking finger 80 is snapped into notch 83 to oppose the normal bias and tendency of spring 74 to force actuator 70 to return to the first cavity end. Moreover, the detent tooth 76 is moved towards the piston 2. Accordingly, as the physician rotates the piston, the bias of spring 74 will move detent tooth 76 into receipt by successive ones of the pair of grooves 3 formed in piston 2 after each 180° rotation thereof for the purpose and advantage that were previously described.

It will be apparent that while a preferred embodiment of the invention has been shown and described, various modifications and changes may be made without departing from the true spirit and scope of the invention. It is to be recognized that once the linear-to-vernier syringe is assembled in the manner earlier disclosed, the syringe is automatically placed in the incrementally rotated mode of operation to provide increased safety and prevent an excessive amount of material from being accidentally or unknowingly infused from the syringe cylinder. Moreover, by virtue of the present invention, a physician need not constantly visually monitor the syringe when in the incrementally rotated mode. The physician may feel and/or hear the resulting locking sound each time that detent tooth 42 is received in a locking groove 3. Therefore, the physician can accurately determine the volume of material infused without being unecessarily distrated from his patient.

Having thus set forth a preferred embodiment of the present invention, what is claimed is:

1. A syringe assembly comprising:
   a cylinder from which a volume of material can be dispensed;
   piston means to be inserted in and moveable through said cylinder for expulsing material therefrom; and
   collar means having a hole for receiving said piston means therethrough, said collar means being removably connected to said cylinder to support and align said piston means for movement through said cylinder, said collar means also including:
   at least one exterior face;
   an interior core spaced from said face;
   an access opening formed in said face through which an end of said cylinder may be inserted, said collar means being removably connected to said cylinder when said cylinder is inserted through said access opening and rotated through the space between said exterior face and said interior core;
   a catch member;
   a seat formed in said interior core into which said catch member may be moved; and
   position control means communicating with said catch member and extending through said collar means to a manually accessible position thereof at which to control the movement of said catch member relative to said seat, said position control means being operable to move said catch member either into said seat in said core to permit the rotation of said cylinder end and the connection or disconnection of said collar means to or from said cylinder or out of said seat and into the space between said exterior face said interior core to block the rotation of said cylinder end and prevent the disconnection of said collar means from said cylinder.

2. The syringe assembly recited in claim 1, wherein said piston means and the hole in said collar means for receiving said piston means are threaded, such that a rotation of said piston means relative to said collar means causes a corresponding linear, axial movement of said piston means through said cylinder.

3. The syringe assembly recited in claim 4, wherein said position control means includes a pin connected to said catch member and movable through a slot formed in said collar means, the movement of said pin in one direction through said slot causing a corresponding movement of said catch member into said seat, and the movement of said pin in an opposite direction through said slot causing a corresponding movement of said catch member out of said seat and into the space between the exterior face and interior core of said collar means.

4. A syringe assembly having means by which a measured volume of material can be dispensed either freely or in discrete, calibrated steps, said syringe comprising:
   a cylinder from which a volume of material can be removed;
   piston means to be rotated in and movable axially through said cylinder for dispensing material therefrom, said piston means having a groove extending longitudinally therealong; and
   means to selectively control the movement of said piston means through said cylinder including a detent tooth movable into and removable from the longitudinally extending groove of said piston means;
   said piston means being rotated continuously and moved axially through said cylinder to freely dispense material therefrom when said detent tooth is removed from said groove, or said piston means being rotated incrementally and moved axially through said cylinder to dispense material therefrom in discrete steps when said tooth is successively removed from and returned to said groove.

5. The syringe assembly recited in claim 4, further comprising collar means having a hole for receiving said piston means therethrough, said collar means connected to said cylinder to support and align said piston means for movement through said cylinder, and said piston means and the hole in said collar means being threaded, such that a rotation of said piston means relative to said collar means causes a corresponding axial movement of said piston means through said cylinder.

6. The syringe assembly recited in claim 5, said collar means comprising a detent arm having said detent tooth located at one end thereof and being mounted for rotation within said collar means for moving said detent tooth into and out of the groove in said piston means.

7. The syringe assembly recited in claim 6, wherein said detent arm is located in and rotatable through a cavity formed in said collar means.

8. The syringe assembly recited in claim 6, said collar means further comprising stop means being moveable to a location between said detent tooth and said piston means to prevent the return of said tooth to said groove after said detent arm has rotated said detent tooth out of said groove, so that said piston means may be continuously rotated and axially moved through said cylinder until said stop means is moved out of the way of said detent tooth and said tooth is returned to said groove.

9. The syringe assembly recited in claim 8, said collar means further comprising a selector switch interconnected with said stop means and being manually accessible so as to be moved to either of a first or second switch position, the movement of said selector switch to the first switch position causing a corresponding movement of said stop means to a location between said detent tooth and said piston means, and the movement of said selector switch to the second switch position causing a corresponding movement of said stop means out of the way of said detent tooth.

10. The syringe assembly recited in claim 6, said collar means further comprising a push button interconnected with the second end of said detent arm and being manually accessible for causing the rotation of said detent arm and the movement of said detent tooth into and out of the groove in said piston means.

11. The syringe assembly recited in claim 10, said collar means further comprising a compression spring interconnected with said push button for controlling the rotation of said detent arm, a depression of said button against the normal bias of said spring causing a rotation of said detent arm and a movement of said detent tooth out of the groove in said piston means so that said piston means may be rotated and moved axially a corresponding distance through said cylinder for dispensing a particular volume of material until said push button is released and said detent tooth is returned to said groove.

12. The syringe assembly recited in claim 4, further comprising compression spring means for biasing said detent tooth for movement into and out of said groove depending upon whether said spring means is compressed or relaxed, push button means being manually accessible and interfaced with said spring means for alternatingly compressing and relaxing said spring means, and releasable locking means to prevent the movement of said detent tooth out of said groove when said push button means is operated and said spring means is compressed.

13. The syringe assembly recited in claim 12, wherein said detent tooth, said spring means, and said push button means are integrally connected as a single continuous piece.

14. A syringe assembly comprising:
   a cylinder from which a volume of material can be dispensed;
   piston means to be rotated in and moveable axially through said cylinder for expulsing material therefrom, said piston means having a groove extending longitudinally therealong;
   collar means having a hole for receiving said piston means therethrough, said collar means also having an access opening through which to receive one end of said cylinder so that said collar means may be removably connected to said cylinder and said piston means may be supported for rotation and axial movement, said collar means further having a catch member which is movable into said access opening to block the disconnection of said cylinder from said collar means, and pin means connected to said catch member and extending through said collar means to a manually accessible piston at which to control the movement of said catch member relative to said access opening; and
   means movable into and out of said groove in said piston means to selectively control the rotational and axial movement of said piston means through said cylinder, such that a measured volume of material can be dispensed either continuously or in discrete, calibrated increments.

* * * * *